US009877755B2

(12) United States Patent
Sampath et al.

(10) Patent No.: US 9,877,755 B2
(45) Date of Patent: Jan. 30, 2018

(54) ORTHOPEDIC APPARATUS FOR CORRECTING ROTATIONAL BONE DEFORMITIES AND METHOD FOR USING THE ORTHOPEDIC APPARATUS

(71) Applicants: Jayanth Sundar Sampath, Quebec (CA); Fady Rayes, Vaudreuil-Dorion (CA); Ariel Ricardo Dujovne, Cote St Luc (CA)

(72) Inventors: Jayanth Sundar Sampath, Quebec (CA); Fady Rayes, Vaudreuil-Dorion (CA); Ariel Ricardo Dujovne, Cote St Luc (CA)

(73) Assignee: Pega Medical, Inc., Quebec (CA)

( * ) Notice: Subject to any disclaimer, the term of this patent is extended or adjusted under 35 U.S.C. 154(b) by 231 days.

(21) Appl. No.: 14/216,527

(22) Filed: Mar. 17, 2014

(65) Prior Publication Data

US 2015/0257803 A1 Sep. 17, 2015

(51) Int. Cl.
*A61B 17/80* (2006.01)

(52) U.S. Cl.
CPC ...... *A61B 17/8023* (2013.01); *A61B 17/8004* (2013.01); *A61B 17/809* (2013.01); *A61B 17/8057* (2013.01); *A61B 17/8061* (2013.01)

(58) Field of Classification Search
CPC ... A61B 17/80; A61B 17/809; A61B 17/8004; A61B 17/8023; A61B 17/8061

USPC ..................... 606/70, 71, 280–299
See application file for complete search history.

(56) References Cited

U.S. PATENT DOCUMENTS

| | | | |
|---|---|---|---|
| 5,681,313 A * | 10/1997 | Diez ................. | A61B 17/8004 606/282 |
| 6,053,919 A * | 4/2000 | Talos ................. | A61B 17/8071 606/300 |
| 6,699,249 B2 | 3/2004 | Schlapfer et al. | |
| 6,881,215 B2 | 4/2005 | Assaker et al. | |
| 7,811,312 B2 | 10/2010 | Stevens et al. | |
| 2006/0122606 A1* | 6/2006 | Wolgen ............. | A61B 17/663 606/71 |
| 2006/0142767 A1 | 6/2006 | Green et al. | |
| 2010/0131065 A1 | 5/2010 | Burke | |
| 2010/0137865 A1* | 6/2010 | Frankle ............. | A61B 17/1725 606/64 |

* cited by examiner

*Primary Examiner* — Christopher Beccia
(74) *Attorney, Agent, or Firm* — Polsinelli PC

(57) ABSTRACT

Embodiments of an orthopedic apparatus and method for using the orthopedic apparatus to correct rotational bone deformities are disclosed. Embodiments of the orthopedic apparatus include a stationary segment having a fixed portion engaged to a first bone portion and a track portion engaged to a mobile segment that is engaged to a second bone portion separated by the first bone portion by a growth plate such that the mobile segment migrates over time from a first position along the stationary segment to a second position along the stationary segment in such a way that torsional growth and correction of an angular deformity are promoted.

23 Claims, 11 Drawing Sheets

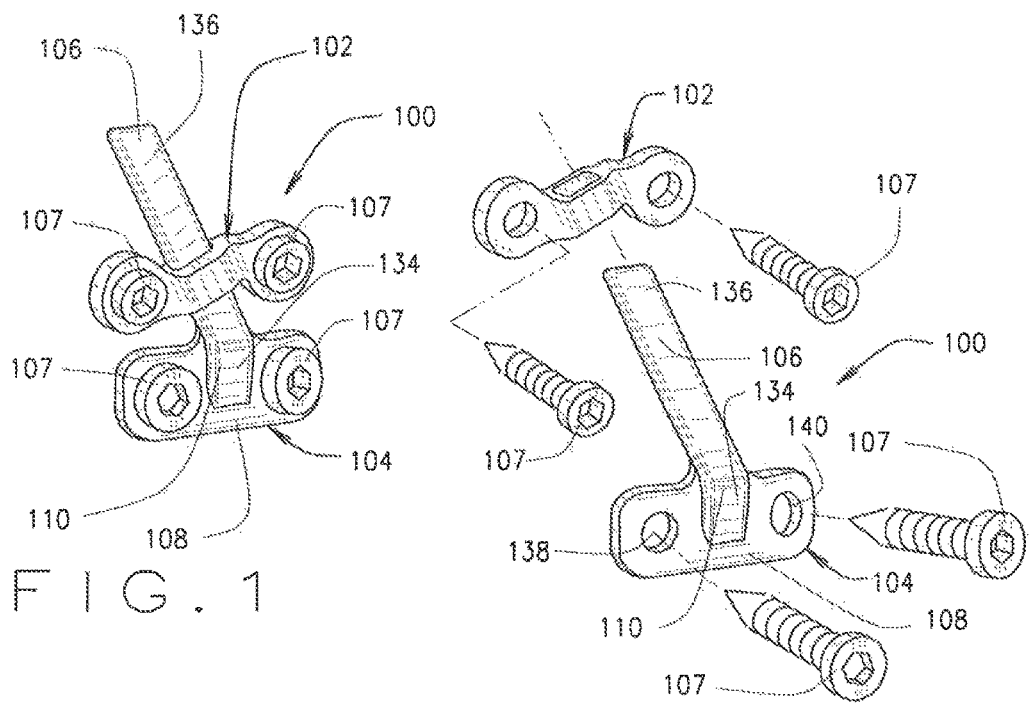
FIG. 1
FIG. 2
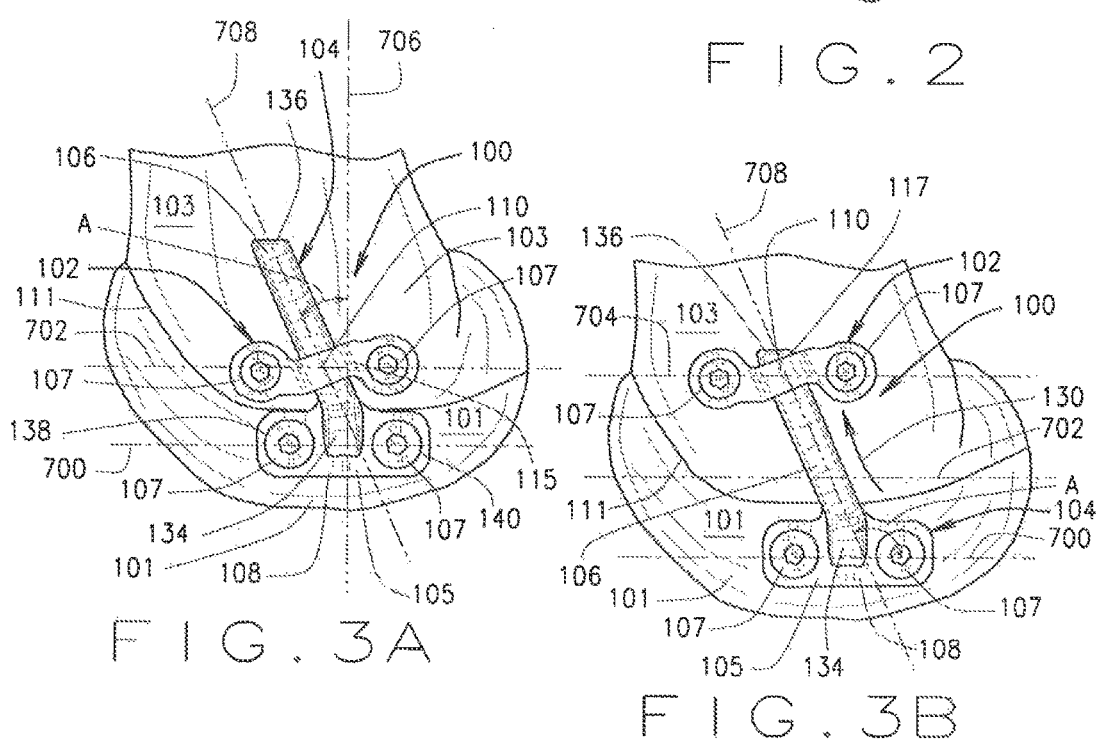
FIG. 3A
FIG. 3B

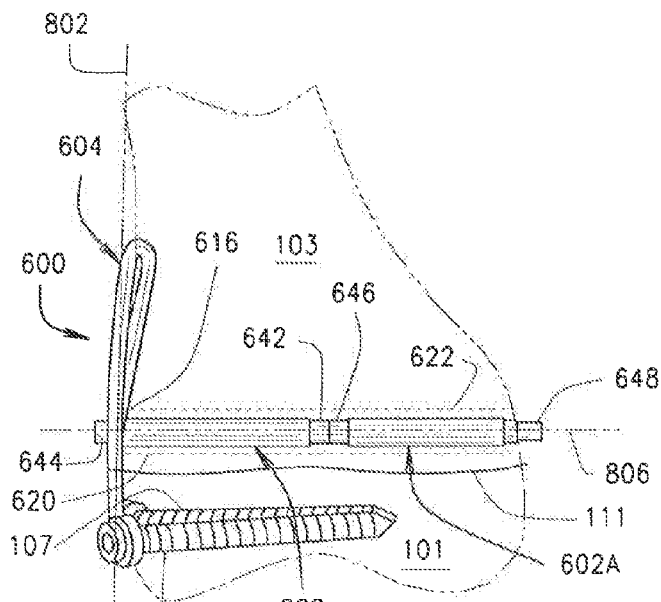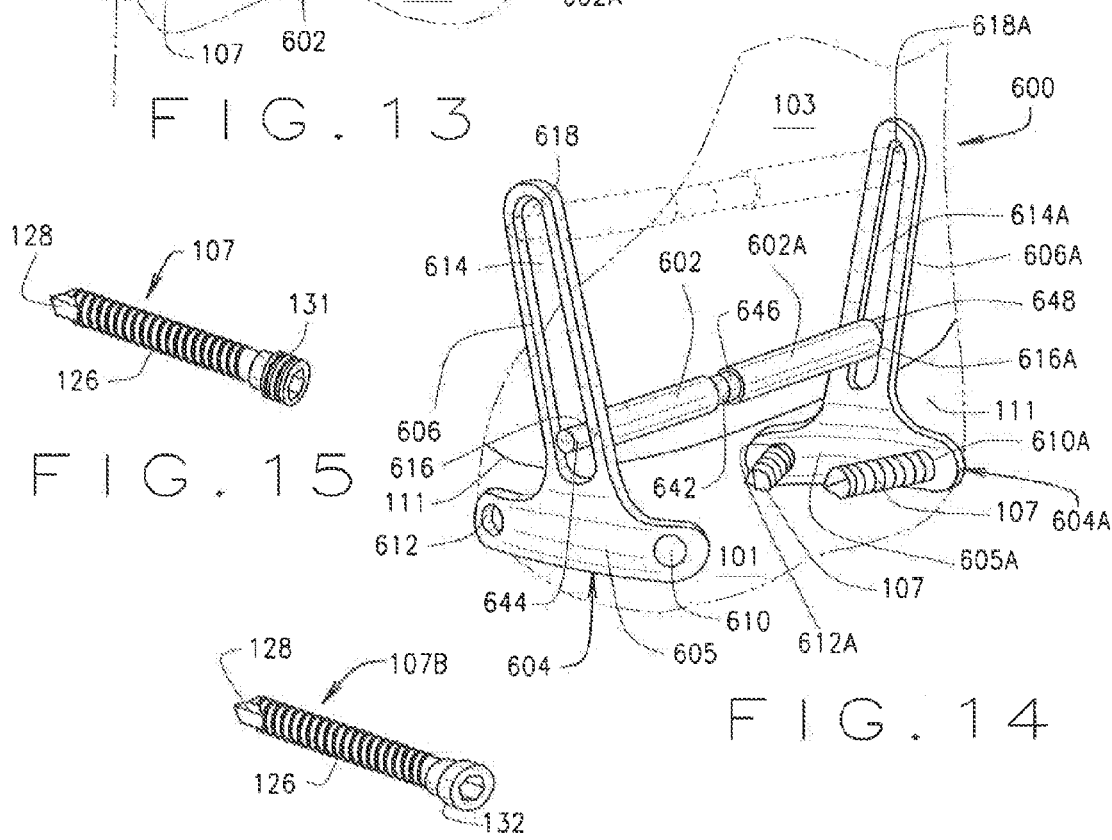

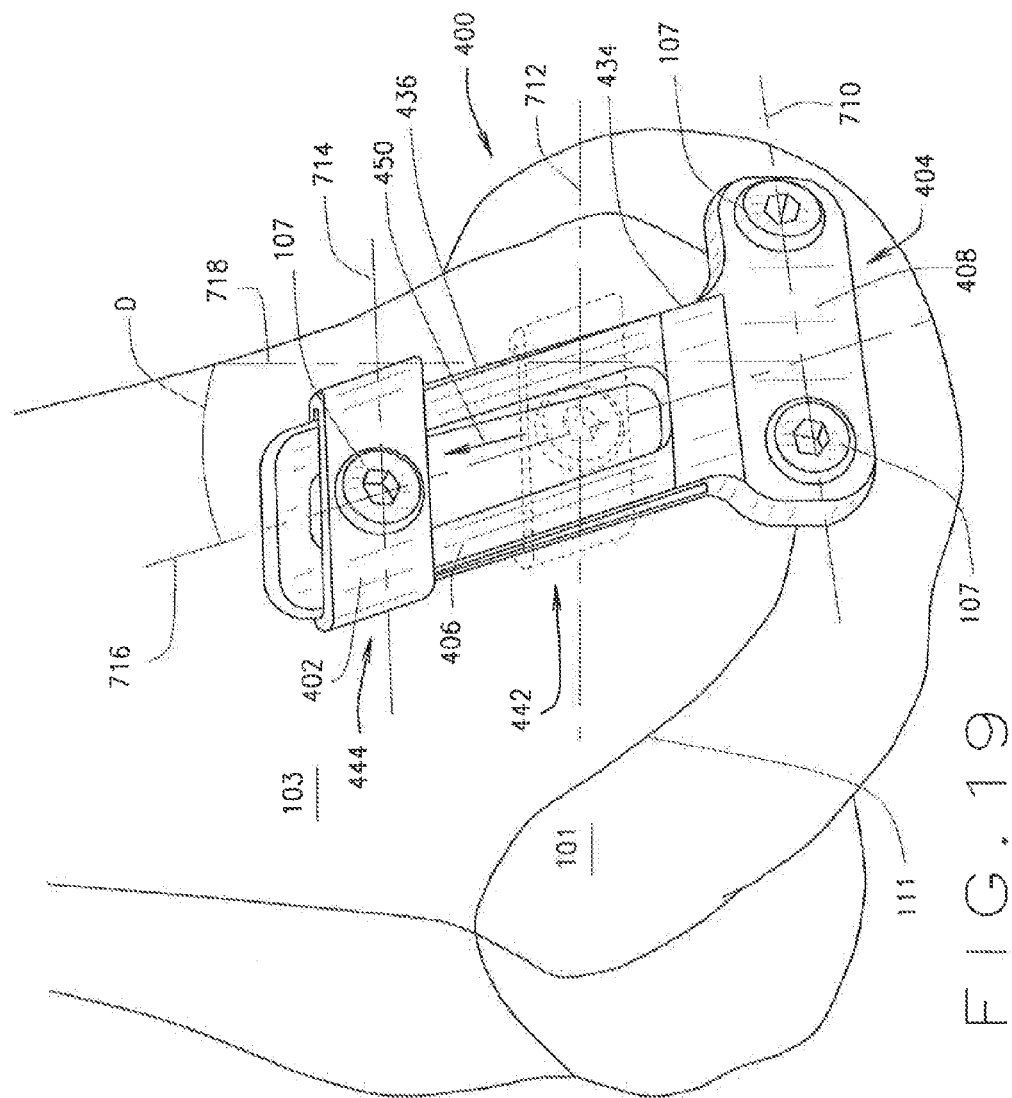

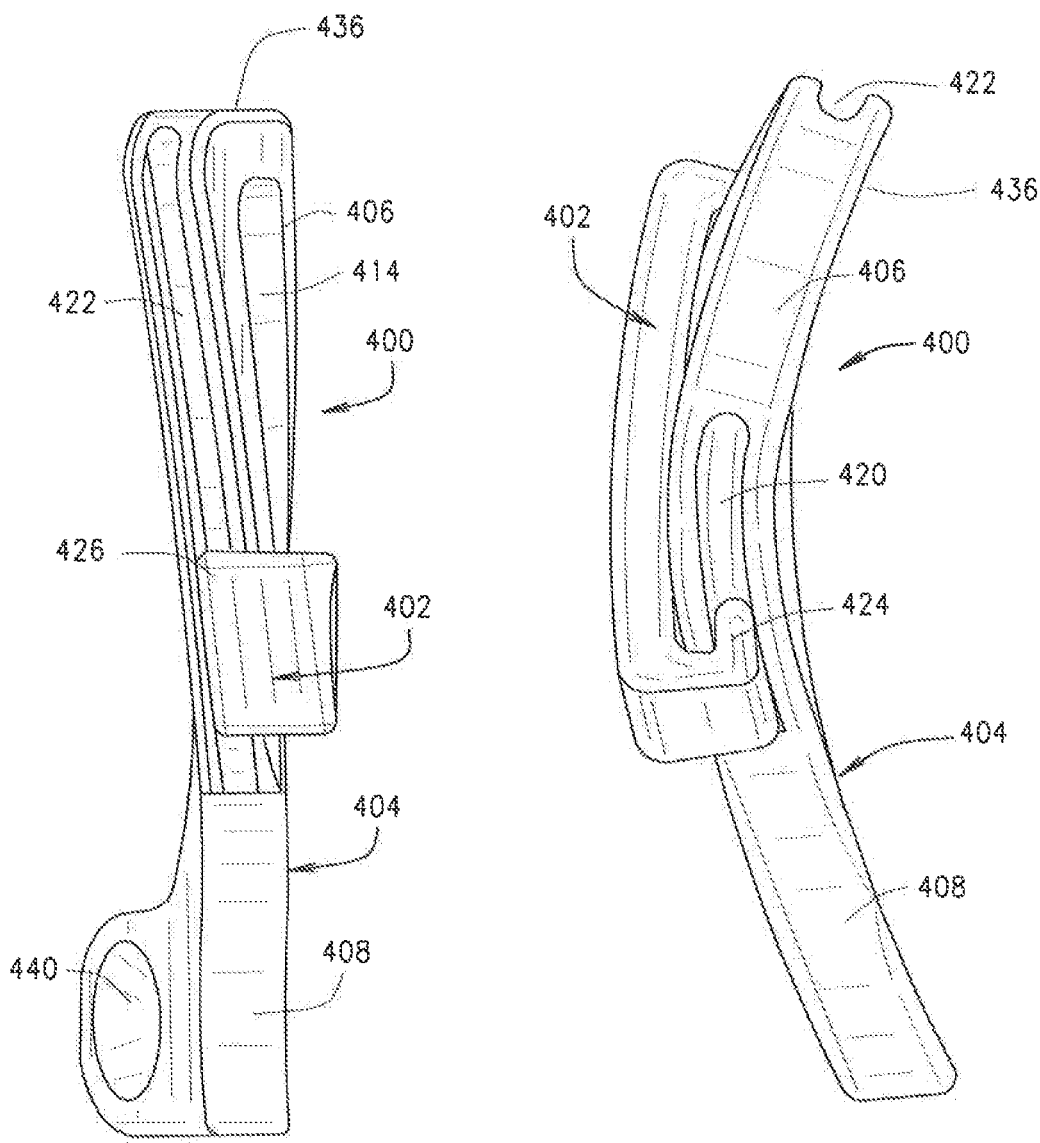

ORTHOPEDIC APPARATUS FOR CORRECTING ROTATIONAL BONE DEFORMITIES AND METHOD FOR USING THE ORTHOPEDIC APPARATUS

FIELD

This document relates to an orthopedic apparatus, and more particularly to an orthopedic apparatus and related method for correcting rotational bone deformities.

BACKGROUND

In orthopedics, rotational deformities of the bone along the lower portions of an individual can change the planar orientation of various respective reference planes for the hip, knee and ankle. For example, abnormal angulation of the femoral neck with respect to the transcondylar axis of the knee is referred to as femoral anteversion. In general, rotational deformities as discussed above may be defined as an abnormal angulation of a bone relative to a longitudinal axis.

It is very common in infants to be born with femoral anteversion due to the position of the fetus inside the womb during pregnancy and can occur in up to 10% of children. In fact, femoral anteversion is the most common cause of children walking with their toes inward (in-toeing) in children older than 3 years of age. Although most rotational bone abnormalities, such as femoral anteversion, are resolved under normal growth and development, a small percentage of cases will continue to suffer from a residual rotational deformity that may later require surgical correction.

One common method of surgical bone realignment to address femoral anteversion is by performing an osteotomy procedure which requires cutting of the bone followed by its realignment to the correct bone orientation. However, osteotomy procedures require making a large incision to create access to the bone for the surgeon to perform the bone cutting and realignment, thereby making the procedure substantially invasive. In addition, the procedure can cause disruption of the adjacent musculature surrounding the bone as well as possibly damaging the neurovascular structures. Procedures to cut and realign bones are associated with a long and painful rehabilitation period that can last several months. The cut bone ends may not heal adequately and in such cases, further surgery may be necessary. Implant failure is also a well documented complication of osteotomies. Another concern is the accidental damage to the growth plate that can occur during the surgical realignment procedure, which can later inhibit healthy and normal limb growth. As such, current surgical bone realignment apparatuses and methods require a relatively invasive procedure be performed to correct rotational bone deformities. An alternative to invasive osteotomies is the use of guided growth through a minimally invasive device.

SUMMARY

In one aspect, an orthopedic apparatus may include a stationary segment having a fixed portion oriented at a first longitudinal axis in perpendicular relation to a latitudinal axis, wherein the fixed portion is configured to engage a first portion of a bone. The stationary segment further includes a track portion configured to extend from the fixed portion along an axis at a predetermined angle from the fixed portion. In addition, a mobile segment is coupled to the track portion of the stationary segment and a plurality of fastening members provided for engaging the stationary segment to the first portion of the bone and the mobile segment to a second portion of the bone. In this manner, the stationary segment and the mobile segment are engaged to the respective first and second portions of the bone separated by a growth plate to promote a torsional growth of the growth plate and correct angular deformation.

In another aspect, an orthopedic apparatus may include a first stationary segment having a first fixed portion oriented at a first longitudinal axis in perpendicular relation to a first latitudinal axis, wherein the first fixed portion is configured to engage a first bone portion. The stationary segment may include a first track portion configured to extend from the first fixed portion along a first axis at a first predetermined angle from the first fixed portion, wherein the first track portion defines a first narrow slot. In addition, the orthopedic apparatus may include a second stationary segment having a second fixed portion oriented along a second longitudinal axis in perpendicular relation to a second latitudinal axis, wherein the second fixed portion is configured to engage the first bone portion and a second track portion configured to extend from the second fixed portion along a second axis at a second predetermined angle from the second fixed portion. The second track portion also defines a second narrow slot. In addition, a plurality of fastening members are provided for engaging the first and second stationary segments to the first bone portion. A first mobile connector is received through the first narrow slot and disposed within a channel defined through a second bone portion and a second mobile connector is received through the second narrow slot and disposed within the channel, wherein the first mobile connector engages the second mobile connector through the channel.

In another aspect, an orthopedic apparatus may include a stationary segment having a fixed portion configured to engage a first bone portion. The stationary segment further includes a track portion formed along the body of the stationary segment defining a helicoidal path. In addition, a mobile segment having a matching helicoidal path is coupled to the track portion of the stationary segment and a plurality of fastening members provided for engaging the stationary segment to a first portion of a bone and the mobile segment to a second portion of the bone. In this manner, the stationary segment and the mobile segment are engaged to the first and second portions of the bone that are separated by a growth plate to promote a torsional growth of the growth plate and correct angular deformation.

In another aspect, a method of correcting a bone deformity may include securing a stationary segment to a first bone portion, coupling a mobile segment to the track portion of the stationary segment, and securing the mobile segment to a second bone portion. The stationary segment includes a fixed portion oriented at a first longitudinal axis in perpendicular relation to a latitudinal axis, wherein the fixed portion is configured to engage the first bone portion and a track portion configured to extend from the fixed portion along an axis at a predetermined angle or pitch from the fixed portion. In addition, the first bone portion and the second bone portion are separated by a growth plate such that torsional growth of the growth plate is promoted.

In yet another aspect, a method of correcting a bone deformity may include engaging a first stationary segment to a first bone portion, forming a channel through a second bone portion, engaging a second stationary segment to the first bone portion, inserting a first mobile connector through a first narrow slot and into the channel, and inserting a second mobile connector through a second narrow slot and into the channel such that the first mobile connector is engaged to the second mobile connector within the channel. The first stationary segment includes a first fixed portion oriented at a first longitudinal axis in perpendicular relation to a first latitudinal axis and a first track portion configured to extend from the first fixed portion along a first axis at a first predetermined angle from the first fixed portion. The first track portion further defines a first narrow slot. In addition, the first fixed portion is configured to engage the second bone portion. The second stationary segment includes a second fixed portion oriented at a second longitudinal axis in perpendicular relation to a second latitudinal axis and a second track portion configured to extend from the second fixed portion along a second axis at a second predetermined angle from the second fixed portion, wherein the second track portion defines a second narrow slot. In addition, the second fixed portion is configured to engage the second bone portion.

Additional objectives, advantages and novel features will be set forth in the description which follows or will become apparent to those skilled in the art upon examination of the drawings and detailed description which follows.

BRIEF DESCRIPTION OF THE DRAWINGS

FIG. 1 is a perspective view of a first embodiment of an orthopedic apparatus;

FIG. 2 is an exploded view of the orthopedic apparatus of FIG. 1;

FIGS. 3A and 3B illustrate the sequence of operation for the orthopedic apparatus of FIG. 1;

FIG. 13 is a side view of the first stationary segment shown in FIG. 12 engaged to a bone though a first mobile connector for the orthopedic apparatus of FIG. 11;

FIG. 14 is a perspective view of the first stationary segment coupled to a second stationary segment through first mobile connector engaged to a second mobile connector for the orthopedic apparatus of FIG. 11;

FIG. 15 is a perspective view of one embodiment of a fastening member used with the orthopedic apparatuses of FIGS. 1, 8 and 11;

FIG. 16 is a perspective view of another embodiment of the fastening member used with the orthopedic apparatuses of FIGS. 1, 8 and 11;

FIG. 19 is a perspective view of the stationary segment and mobile segment coupled together and engaged to a bone for the orthopedic apparatus of FIG. 8;

FIG. 20 is a side view of the mobile segment coupled to the stationary segment for the orthopedic apparatus of FIG. 8;

FIG. 21 is a perspective view of the mobile segment coupled to the stationary segment for the orthopedic apparatus of FIG. 8;

Corresponding reference characters indicate corresponding elements among the various views of the drawings. The headings used in the figures should not be interpreted to limit the scope of the claims.

DETAILED DESCRIPTION

As described herein, embodiments of an orthopedic apparatus and method of use thereof are disclosed that allow for correcting rotational bone deformities in which the orthopedic apparatus includes a stationary segment having an angled or helicoidal track portion configured to engage a mobile segment for allowing the mobile segment to migrate along the track portion over time relative to the stationary segment as the bone grows over time. In one aspect, the orthopedic apparatus is directed a single mobile and stationary segment arrangement in which a single mobile segment is coupled to a single stationary segment engaged to a first portion of a bone, while the mobile segment is engaged to a second portion of the bone separated from the first portion of the bone by a growth plate for migration of the mobile segment along the stationary segment over time in order to promote torsional growth of the growth plate. In another aspect, the orthopedic apparatus is directed to a dual mobile and stationary segments engaged to different portions of the bone separated by the growth plate such that migration of the dual mobile segments also promotes torsional growth of the growth plate over time.

Figure 4:
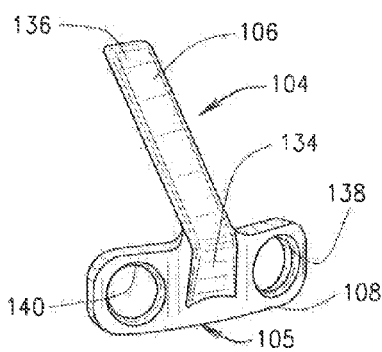
FIG. 4 is a perspective view of an embodiment of a stationary segment for use with the orthopedic apparatus of FIG. 1.

Referring to the drawings, embodiments of the orthopedic apparatus are illustrated and generally indicated as 100, 400, and 600 and in FIGS. 1-33. In general, as shown in FIGS. 1 and 2, a first embodiment of the orthopedic apparatus, designated 100, includes a mobile segment 102 coupled to a stationary segment 104 with a plurality of fastening members 107 that are configured to secure respective portions of the mobile segment 102 and stationary segment 104 to different portions of a bone for a mammalian body. In particular, one embodiment of the stationary segment 104 shown in FIGS. 1, 2, and 4, designated 104, includes a substantially angular-shaped body 105 that defines an elongated track portion 106 configured to be coupled to the mobile segment 102 (FIGS. 1 and 2) and a fixed portion 108 secured to a portion of the bone for correcting the bone deformity. As shown, the track portion 106 defines a straight proximal part 134 integral or attached to the fixed portion 108 and an angled distal part 136 that extends at a predetermined angle relative to the proximal part 134 of the track portion 106. In addition, the fixed portion 108 defines a pair of openings 138 and 140 configured to receive the fastening members 107 as shown in FIGS. 2 and 4.

One method of assembling of the orthopedic apparatus 100 is shown in FIGS. 1, 2 and 3A. As illustrated, the orthopedic apparatus 100 may be assembled by coupling the mobile segment 102 to the track portion 106 of the stationary segment 104, in which the stationary segment 104 is secured to a first bone portion 101 and the mobile segment 102 is secured to a second bone portion 103 separated from the first bone portion 101 by a growth plate 111. For example, the fixed portion 108 of the stationary segment 104 can be secured to the first bone portion 101 using securing members 107 (FIG. 3B) along a first longitudinal axis 700 such that the angled distal part 136 of the track portion 106 extends from the proximal part 134 along an axis 708 at a predetermined angle A, which in some embodiments may be 45 degrees relative to latitudinal axis 706. However, predetermined angle A of the track portion 106 relative to the latitudinal axis 706 may range between 1 to 89 degrees. In addition, the mobile segment 102 may be coupled to the track portion 106 and secured to the second bone portion 103 using securing members 107.

As shown in FIG. 3B, the mobile segment 102 coupled to the track portion 106 of the stationary segment 104 will migrate along the pathway 130 defined by axis 708 of track portion 106 from a first position along longitudinal axis 702 to a second position along longitudinal axis 704 as the first and second bone portions 101 and 103 grow over time relative to the growth plate 111. The rate the mobile segment 102 migrates along the track portion 106 is dependent on the rate of growth of the first and second bone portions 101 and 103 secured to the mobile segment 102 and stationary segment 104 of the orthopedic apparatus 100, respectively. In addition, the migration of the mobile segment 102 along the track portion 106 of the stationary segment 104 guides the growth of the growth plate 111.

Figure 5:
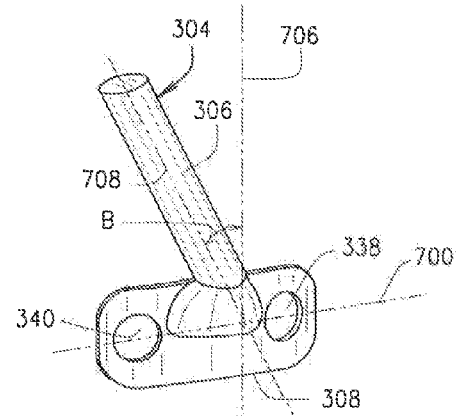
FIG. 5 is a perspective view of another embodiment of the stationary segment for use with the orthopedic apparatus of FIG. 1.

Referring back to FIG. 4, in one embodiment of the stationary segment 104, the track portion 106 may have a generally rectangular cross-sectional configuration. Referring to FIG. 5, in another embodiment of the stationary segment, designated 304, stationary segment 304 includes a track portion 306 having a generally circular cross-sectional configuration that extends outwardly from the fixed portion 308 at predetermined angle B. For example, the fixed portion 308 may be aligned along the first longitudinal axis 700 with the first latitudinal axis 706 in perpendicular relation to the first longitudinal axis 700 with the track portion 306 extending from the fixed portion 308 along axis 708 at a predetermined angle B relative to the first latitudinal axis 706. In some embodiments of the stationary segment 104, predetermined angle B may range between 1 to 89 degrees. The track follows a substantially linear path, but the track can also follow a helicoidal path with a given pitch to create torsion. Similar to the embodiment of fixed portion 108, the fixed portion 308 also defines a first opening 338 and a second opening 340 configured to respective fastening members 107 to secure the fixed portion 308 to a portion of the bone.

As shown in FIGS. 1-4, and 6 one embodiment of the mobile segment 102 includes a substantially angular-shaped segment body 109 that defines a guide portion 110 having a first ring portion 112 and a second ring portion 114 extending substantially in opposite directions from either end of the guide portion 110. As shown, the mobile segment 102 is configured such that the guide portion 110 extends along a longitudinal axis 900, while the upper part of the first ring portion 112 is formed adjacent a parallel plane 902 and the lower part of the second ring portion 114 is formed adjacent another parallel plane 904. In addition, the first ring portion 112 extends along an axis 908 and second ring portion 114 extends along a parallel axis 910. In some embodiments, the guide portion 110 may define a generally rectangular-shaped center aperture 124 similar to the generally rectangular-shaped center aperture 224 (FIG. 7) configured to receive the track portion 106, which also forms substantially the same rectangular-shaped cross-sectional configuration to facilitate the coupling of the mobile segment 102 to the stationary segment 104. To secure the mobile segment 102 to the second bone portion 103, the first ring portion 112 defines a first aperture 116 and the second ring portion 114 defines a second aperture 118 with each of the apertures 116 and 118 configured to receive a respective fastening member 107 to secure the mobile segment 102 to the second bone portion 103 during a surgical procedure as shall be discussed in greater detail below. The angled position of the first aperture 116 along axis 910 relative to the second aperture 118 along axis 908 permits the first and second apertures 116 and 118 to maintain a substantially parallel orientation to axis 700 of the fixed portion 108 during migration of the mobile portion 102 illustrated in FIG. 3B.

Generally, growth of mammalian long bones occurs at the growth plate 111 (also term physis), which is complex in its anatomy and function. In the physiological context, cells in the physis are capable of division in response to hormonal, chemical and mechanical influences. The exact mechanisms by which these processes occur are yet to be fully understood; however, growth occurs through continued division of cartilage cells in the physis, which is subsequently converted into bone. Growth plates 111 have the ability to lengthen the bone along an axis that bears a fixed relationship to known anatomical and mechanical axes of limbs. Although there are minor variations between individuals, the general shape of normal long bones is the result of the ability of growth plates 111 to lay down new bone along a predetermined axis along the coronal, sagittal and axial planes.

In general, as shown in FIGS. 3A and 3B, the stationary segment 104 is secured to the first bone portion 101 on one side of the growth plate 111 and the mobile segment is secured to the second bone portion 103 on the opposite side of the growth plate 111. The angular-shaped body 105 of the stationary segment 104 is positioned at an angle relative to the growing or long axis 706 of the bone. As the physis lays down new bone, the mobile segment 102 migrates away from the stationary segment 104 along axis 708 which is at an angle to the axis 706 of the bone, which is represented by angle B in FIG. 5. This process of migration applies gradual and controlled torsional forces to the growth plate 111. It is known that the growth plate 111 is able to respond to such torsional forces. Studies have also confirmed that the columns of immature cartilage with the growth plate 111 may twist and lay down bone along a new axis. As the mobile segment 102 does not restrict expansion at the growth plate 111, such expansion does not result in growth restriction or angular deformity of the bone. Therefore, as growth progresses the part of the bone secured to the mobile segment 102 twists in relation to the part of the first bone portion 101 secured to the stationary segment 104.

Figure 7:
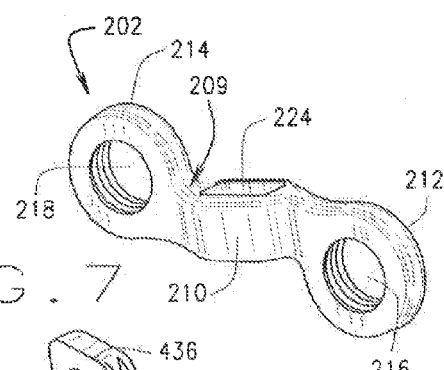
FIG. 7 is a perspective view of another embodiment of the mobile segment for use with the orthopedic apparatus of FIG. 1.

In another embodiment illustrated in FIG. 7, the mobile segment, designated 202, has substantially the same configuration as mobile segment 102 with the same angular-shaped segment body 209. The mobile segment 202 includes a guide portion 210 that defines a generally rectangular-shaped center aperture 224, except the mobile segment 202 includes a first ring portion 212 and a second ring portion 214 that define respective threaded openings 216 and 218 rather than spherical-shaped openings 116 and 118. In one configuration, the mobile segment 102 is configured to be secured by fastening members 107B with the spherical-shaped head 132, while the mobile segment 202 is configured to be secured by fastening members 107A with the threaded distal head 131 as shall be explained in greater detail below.

Figure 8:
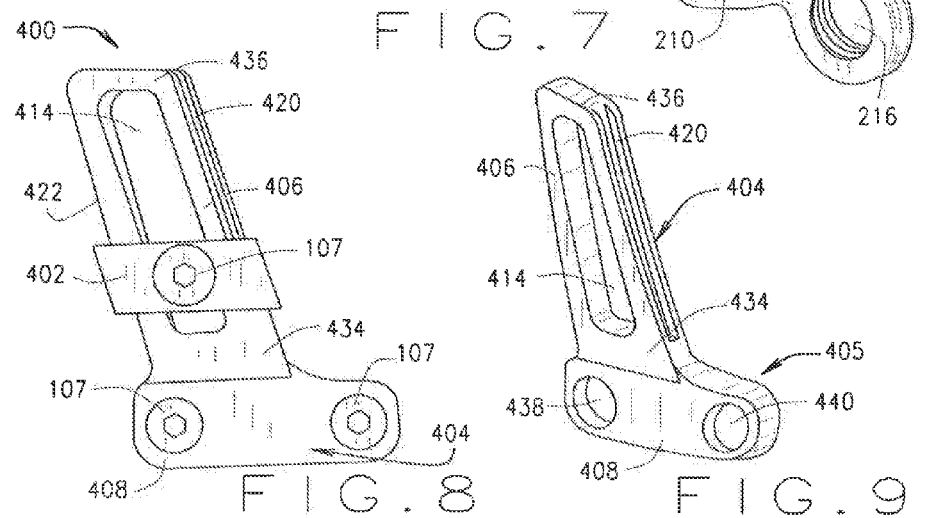
FIG. 8 is a front view of a second embodiment of the orthopedic apparatus showing a mobile segment coupled to a stationary segment.
Figure 9:
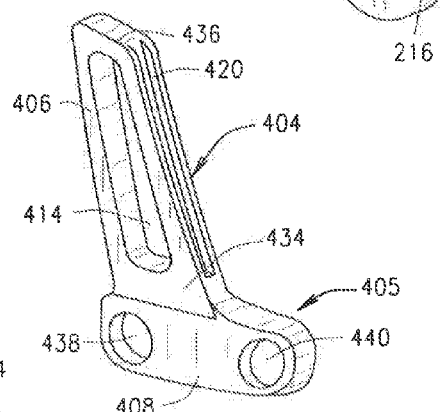
FIG. 9 is a perspective view of the stationary segment for use with the orthopedic apparatus of FIG. 8.
Figure 10:
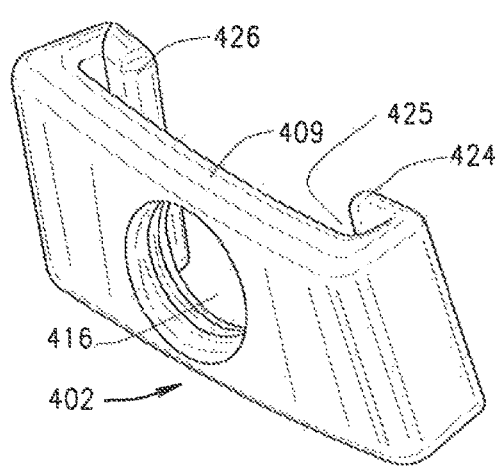
FIG. 10 is a perspective view of the embodiment of the mobile segment for use with the orthopedic apparatus of FIG. 8.

Referring to FIGS. 8-10 and FIGS. 19-33, a second embodiment of orthopedic apparatus, designated 400, is illustrated. As shown in FIG. 8, the orthopedic apparatus 400 includes a stationary segment 404 coupled to a mobile segment 402. As shown specifically in FIGS. 8 and 9, the stationary segment 404 defines a curved-shaped body 405 that includes a fixed portion 408 and a track portion 406 that extends at an angle from the fixed portion 408. In some embodiments, the track portion 406 of the stationary segment 404 is configured to be engaged to the mobile segment 402 and the fixed portion 408 of the stationary segment 404 is configured to be secured to the first bone portion 101 of an individual for correcting a rotational bone deformity as the first and second bone portions 103 grow over time and torsional growth of the growth plate 111 is promoted. As shown, the track portion 406 defines a proximal part 434 integral or attached to the fixed portion 408 and an angled distal part 436 formed at the free end of the track portion 406.

Figure 22:
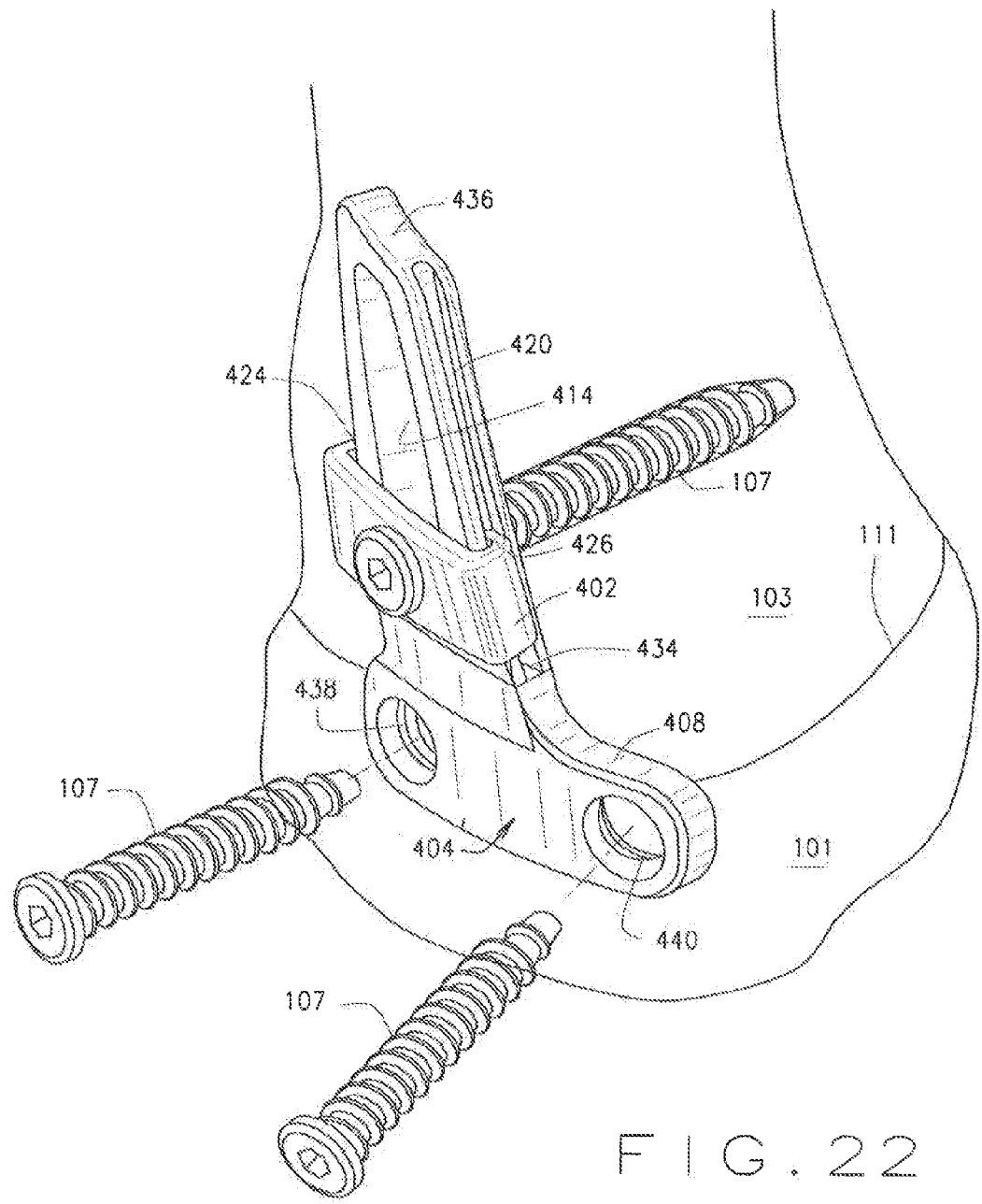
FIG. 22 is a perspective view of the mobile segment coupled to the stationary segment engaged to a bone with fastening members for the orthopedic apparatus of FIG. 8.

Referring to FIGS. 9, 23, 24 and 27, the fixed portion 408 of the stationary segment 404 includes a first opening 438 and a second opening 440 configured to receive respective fastening members 107 (FIG. 8) when securing the stationary segment 404 to the first bone portion 101 (FIG. 19). In addition, the track portion 406 defines a narrow slot 414 configured to allow insertion of a fastening member 107. The fastening member 107 may also be inserted through the opening 416 of the mobile segment 402 as well as the narrow slot 414 of the stationary segment 404, as shown in FIGS. 19 and 22. Referring specifically to FIG. 19, the configuration of the narrow slot 414 and the coupling of the mobile segment 402 with the stationary segment 404 through the fastening member 107 permits the mobile segment 402 to migrate upwardly along the narrow slot 414 from a first position 442 to a second position 444 along the track portion 406 over time as the bone grows as shall be discussed in greater detail below.

Referring to FIGS. 8, 9, 20 and 21, the track portion 406 of the stationary segment 404 further defines opposing first and second grooves 420 and 422 on at least two outer edge portions of the track portion 406. In an aspect, the first and second grooves 420 and 422 may substantially span the perimeter of the track portion 406. In some embodiments, the first and second grooves 420 and 422 are configured to receive in sliding engagement respective first and second retaining members 424 and 426 of the mobile segment 402 when coupling the mobile segment 402 with the stationary segment 404. The first and second grooves 420 and 422 are further configured to guide the mobile segment 402 along the track portion 406 as the mobile segment 402 migrates from the first position 442 to the second position 444 to promote growth of the growth plate 111 and correct angular deformation of the bone.

Figure 23:
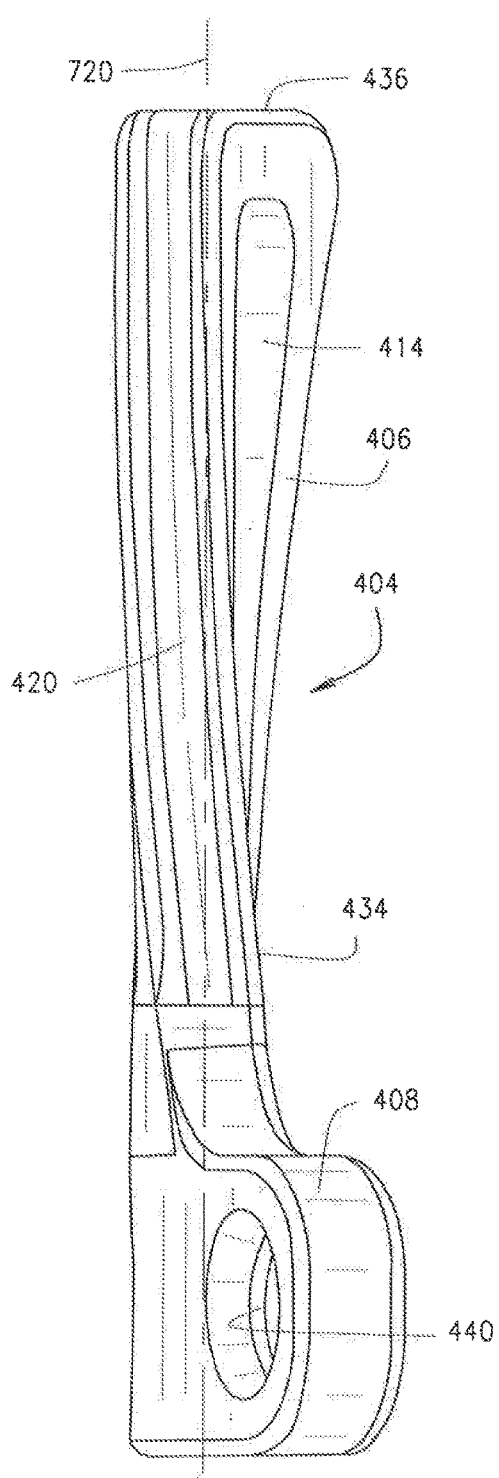
FIG. 23 is a side view of the stationary segment for the orthopedic apparatus of FIG. 8.
Figure 24:
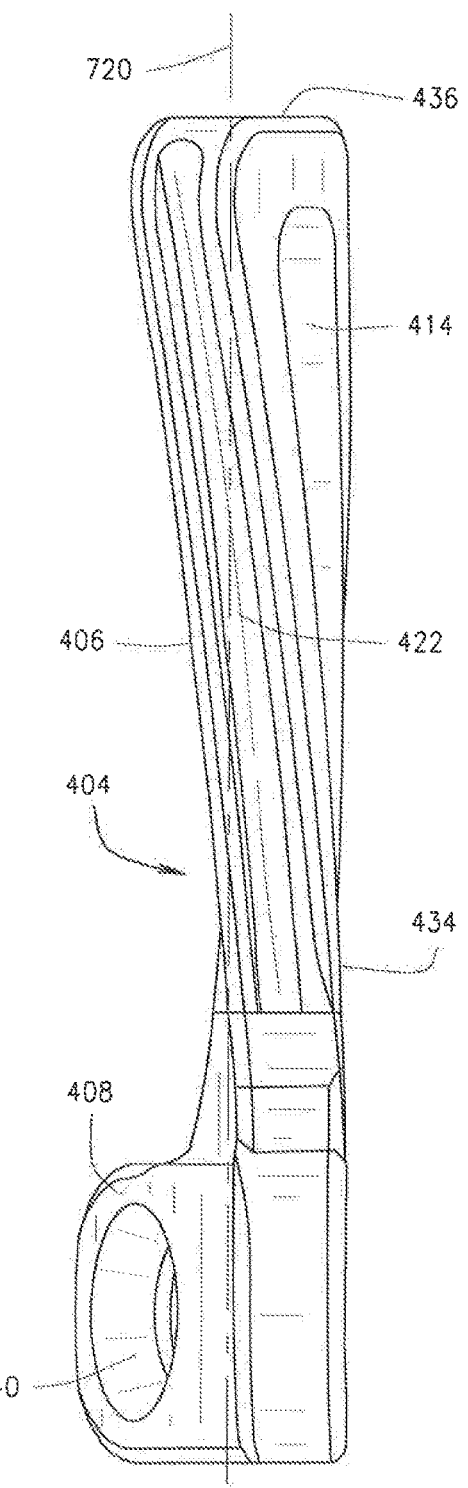
FIG. 24 is an opposing side view of the stationary segment for the orthopedic apparatus of FIG. 8.
Figure 25:
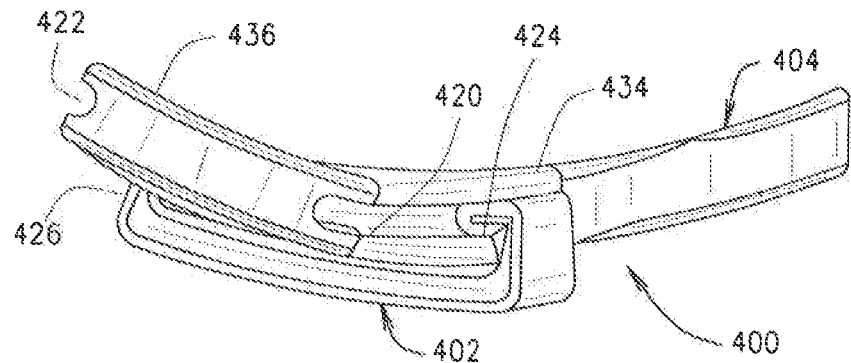
FIG. 25 is a top view of the orthopedic apparatus of FIG. 8 showing the mobile segment initially engaged to the stationary segment prior to migration of the mobile segment.
Figure 26:
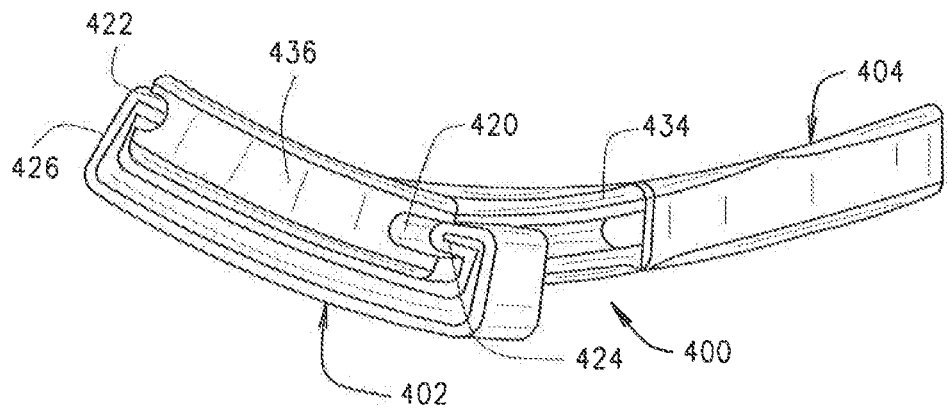
FIG. 26 is a top view of the orthopedic apparatus of FIG. 8 showing the mobile segment having migrated along the stationary segment over time.
Figure 27:
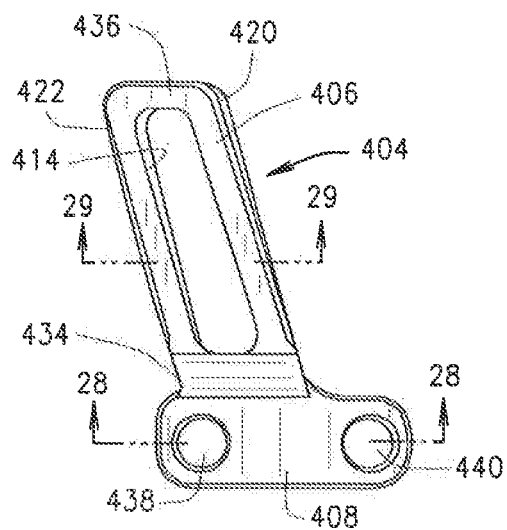
FIG. 27 is a front view of the stationary segment for the orthopedic apparatus of FIG. 8.
Figure 28:
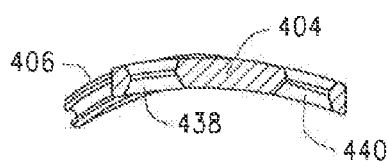
FIG. 28 is a cross-sectional view of the stationary segment taken along line 28-28 of FIG. 27.
Figure 29:
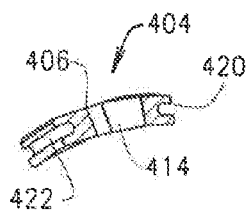
FIG. 29 is a cross-sectional view of the stationary segment taken along line 29-29 of FIG. 27.
Figure 30:
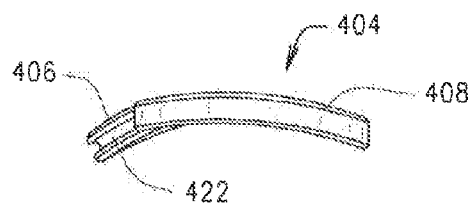
FIG. 30 is a bottom view of the stationary segment for the orthopedic apparatus of FIG. 8.

In some embodiments the stationary segment 404 may define a slightly curved or bowed configuration when viewed in a three-dimensional plane. For example, as shown in FIGS. 23 and 24, the stationary segment 404 is shaped such that the curved body 405 defines a curved or bowed configuration relative to plane 720. In this embodiment, the first groove 420 and second groove 422 define a linear path, but can also follow a helicoidal path with a given pitch to create torsion. In some embodiments, the track portion 406 may be shaped to substantially conform to the structure of the first and second bone portions 101 and 103. As shown, the first and second grooves 420 and 422 and the narrow slot 414 may be sufficiently curved or bow-shaped to follow the general profile of the curved body 405 and track portion 406 of the stationary segment 404. In one aspect, the stationary segment 404 may be curved to abut and follow the curvature of the first bone portion 101 and second bone portion 103. In one embodiment, the first and second grooves 420 and 422 of track portion 406 may have a generally semi-circular cross-sectional configuration. In other embodiments of the stationary segment 404, the track portion 406 may have a generally symmetrical configuration or an asymmetrical cross-sectional configuration. In other embodiments, the stationary segment 404 may also have an irregular cross-sectional configuration.

Figure 31:
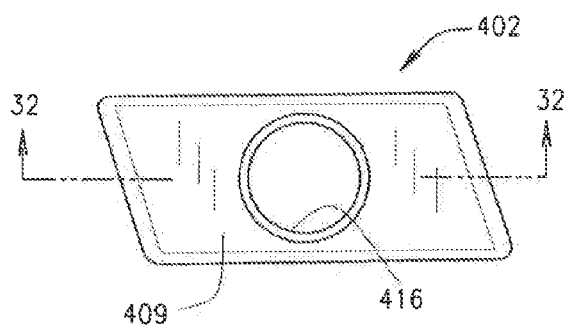
FIG. 31 is a front view of the mobile segment for the orthopedic apparatus of FIG. 8.
Figure 32:
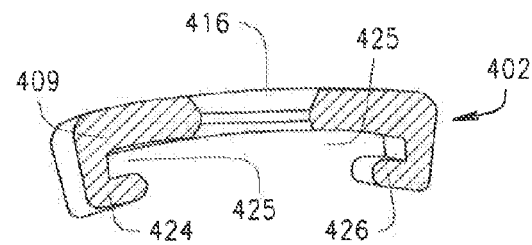
FIG. 32 is a cross-sectional view of the mobile segment taken along lint 32-32 of FIG. 31.
Figure 33:
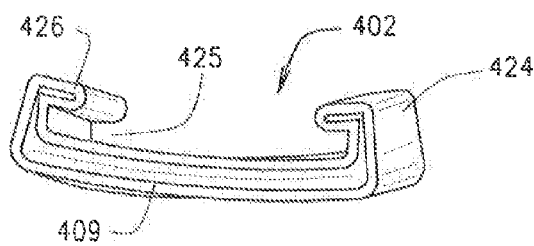
FIG. 33 is an elevated perspective view of the mobile segment for the orthopedic apparatus of FIG. 8.

Referring to FIGS. 10 and 28-33, in some embodiments the mobile segment 402 may define a curved body 409 configured to substantially comport with the general shape of the stationary segment 404. As shown in FIG. 31, in some embodiments the curved body 409 of the mobile segment 402 may have a generally parallelogram-shaped configuration with opposing first and second retaining members 424 and 426 each configured to engage and guide the mobile segment 402 along the first and second grooves 420 and 422, respectively, of the stationary segment 404. As shown, the curved body 409 and the first and second retaining members 424 and 426 of the mobile segment 402 collectively define a slot 425 configured to receive the curved body 405 of the stationary segment 404 when the mobile segment 402 is coupled to the stationary segment 404. The curved body 409 of the mobile segment 402 also defines a central opening 416 configured to receive a fastening member 107 to secure the mobile segment 402 to the second bone portion 103 as shown in FIGS. 19 and 22. As noted above, the curved body 409 of the mobile segment 402 may define a similar curvature to comport the curved body 409 to the track portion 406 of the stationary segment 404.

As shown in FIG. 19, the mobile segment 402 migrates along the linear paths defined by the first and second grooves 420 and 422 and the narrow slot 414 of the track portion 406 as torsional growth of the growth plate 111 is promoted. In one arrangement shown in FIG. 22, the mobile segment 402 may be coupled to the stationary segment 404 by inserting the curved body 405 of the stationary segment 404 through the slot 425 (FIG. 32) defined by the mobile segment 402 such that the first and second retaining members 424 and 426 of the mobile segment 402 are received within the first and second grooves 420 and 422, respectively, of the track portion 406 for the stationary segment 404. Once coupled, a fastening member 107 is inserted through the opening 416 of the mobile segment 402 and the narrow slot 414 of the track portion 406 to engage the mobile segment 402 to the second bone portion 103 as well as the stationary segment 404. This engagement allows the mobile segment 402 to be coupled to the stationary segment 404 in a manner that allows the mobile segment 402 to migrate along the linear paths defined by narrow slot 414 and the first and second grooves 420 and 422. In this arrangement, the mobile segment 402 may be secured to both the stationary segment 404 and the second bone portion 103, while the stationary segment 404 may be secured to the first bone portion 101.

Referring to FIGS. 19 and 22, the orthopedic apparatus 400 may be assembled by coupling the mobile segment 402 to the track portion 406 of the stationary segment 404, in which the stationary segment 404 is secured to the first bone portion 101 and the mobile segment 402 is secured to a second bone portion 103 which are separated from the first bone portion 101 by growth plate 111. For example, the fixed portion 408 of the stationary segment 404 may be secured to the first bone portion 101 using securing members 107 along a first longitudinal axis 710 such that the angled distal part 436 of the track portion 406 extends from the proximal part 434 along an axis 716 at a predetermined angle D (FIG. 19), which in some embodiments may be 45 degrees relative to the latitudinal axis 718. However, predetermined angle D of the track portion 406 relative to the latitudinal axis 718 may range between about 1 to about 89 degrees. In addition, the mobile segment 402 may be coupled to the track portion 406 and secured to the second bone segment portion 103 using a securing member 107.

Referring to FIG. 19, as noted above the mobile segment 402 coupled to the track portion 406 of the stationary segment 404 will migrate over time in direction 450 along the linear pathway defined by axis 716 of track portion 406 from a first position 442 (shown in phantom) along longitudinal axis 712, which is adjacent the proximal part 434 of the track portion 406 (FIG. 25), to a second position 444 along longitudinal axis 714, which is adjacent the distal part 436 of the track portion 406 (FIG. 26), as torsional growth of the growth plate 111 is promoted. The rate the mobile segment 402 migrates along the track portion 406 is dependent on the rate of growth of the first and second bone portions 101 and 103 secured to the mobile segment 402 and stationary segment 404, respectively. In addition, the migration of the mobile segment 402 along the first and second grooves 420 and 422 of the stationary segment 404 guides the growth of the growth plate 111.

Figure 6:
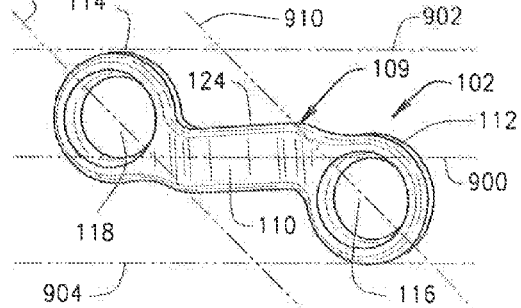
FIG. 6 is a perspective view of an embodiment of a mobile segment for use with the orthopedic apparatus of FIG. 1.

Referring to FIG. 15, one embodiment of the fastening member 107 used to secure the orthopedic apparatus 100 to different portions of the bone may include an elongated threaded body 126 defining a self-tapping distal tip 128 at one end and a threaded proximal head 131 defined at the opposite end of elongated threaded body 126. In some embodiments, the fastening member 107 is configured to engage the embodiment of the mobile segment 202 having first and second ring portions 212 and 214 such that the threaded proximal head 131 of each fastening member 107 is configured to engage respective internal threaded apertures 216 and 218. In another embodiment of the fastening member illustrated in FIG. 16, designated 107B, the fastening member 107B may include the elongated threaded body 126 having the self-tapping distal tip 128 at one end of the elongated threaded body 126 and a spherical proximal head 132 defined at the opposite end thereof. The fastening member 107B is configured to engage the embodiment of the mobile segment 102 having the first and second apertures 116 and 118 defined by respective first and second ring portions 112 and 114 as illustrated in FIG. 6.

Referring back to FIGS. 3A and 3B, one embodiment of a method for using the orthopedic apparatus 100 is illustrated. As shown in FIG. 3A, the guide portion 110 of the mobile segment 102 is coupled to the track portion 106 of the stationary segment 104 such that the mobile segment 102 is positioned at a first position 115 adjacent or proximate to the fixed portion 108 along the track portion 106. Once the mobile segment 102 is coupled to the stationary segment 104 by inserting the track portion 106 through the central aperture 124 of the mobile segment 102, the stationary segment 104 is engaged to the first bone portion 101 by inserting respective fastening members 107 through each respective opening 138 and 140 of the stationary segment 104 such that the fixed portion 108 is fully engaged to the first bone portion 101 and aligned along the first longitudinal plane 700 while the mobile segment 102 is aligned along the second longitudinal plane 702 at the first position 115. Once the stationary segment 104 is affixed to the first bone portion 101, the mobile segment 102 is then secured to the second bone portion 103 on the other side of the growth plate 111 by engaging respective fastening members 107 through first and second openings 116 and 118 such that the mobile segment 102 is located at the first position 115 and substantially aligned along second longitudinal axis 702, while the growth plate 111 is located between axes 700 and 702.

Referring to specifically to FIG. 3A, once the mobile segment 102 is affixed to the second bone portion 103 along the second longitudinal axis 702 and the stationary segment 104 is affixed to the first bone portion 101 at the first longitudinal axis 700 as described above, the mobile segment 102 will be allowed to migrate from the proximal part 134 toward the distal part 136 of the track portion 106 in direction 130 as the bone grows over time. This migration of the mobile segment 102 in direction 130 will continue until the mobile segment 102 reaches a second position 117 defined along the track portion 106 proximate the angled distal part 136 such that the mobile segment 102 is now aligned along a third longitudinal axis 704 shown in FIG. 3B.

Figure 11:
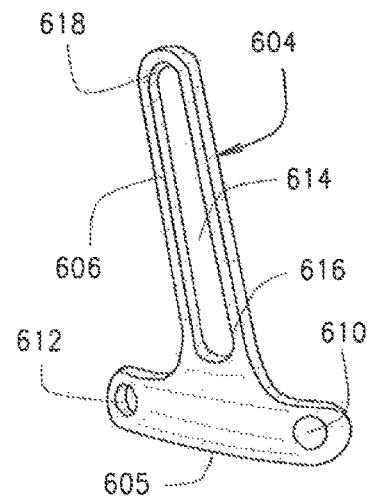
FIG. 11 is a perspective view of a first stationary segment for a third embodiment of the orthopedic apparatus.

Another embodiment of the orthopedic apparatus, designated 600, is illustrated in FIG. 14. The orthopedic apparatus 600 includes a first stationary segment 604 engaged to an identically-shaped second stationary segment 604A through a first mobile connector 602 engaged to a second mobile connector 602A, respectively. As shown in FIG. 11, the first stationary segment 604 includes a first fixed portion 605 and a first track portion 606 that extends at an angle from the first fixed portion 605. The first fixed portion 605 includes a first opening 610 and a second opening 612 configured to receive respective fastening members 107 when engaging the first stationary segment 604 to the bone. In addition, the first track portion 606 defines a first narrow slot 614 configured to receive the first mobile connector 602 and permit the first mobile connector 602 (FIG. 12) to migrate along the first narrow slot 614 from a first position 616 to a second position 618 defined by first track portion 606 over time as the bone grows (FIG. 12) as shall be discussed in greater detail below.

Referring back to FIG. 14, the second stationary segment 604A of the orthopedic apparatus 600 has substantially the same configuration as first stationary segment 604. In particular, the second stationary segment 604A includes a second fixed portion 605A and a second track portion 606A that extends at a predetermined angle from the second fixed portion 605A. The second fixed portion 605A includes a first opening 610A and a second opening 612A configured to receive respective fastening members 107 when engaging the second stationary segment 604A to the bone. In addition, the second track portion 606A also defines a second narrow slot 614A configured to receive the second mobile connector 602A but also allow the second mobile connector 602A to migrate along the second narrow slot 614A from a first position 616A to a second position 618A defined by second track portion 606A as the bone grows over time in similar fashion as the migration of the first mobile connector 602 along the first narrow slot 614 of the first track portion 606. In another embodiment, first and second mobile connectors 602 and 602A may also be one unitary connector.

Figure 12:
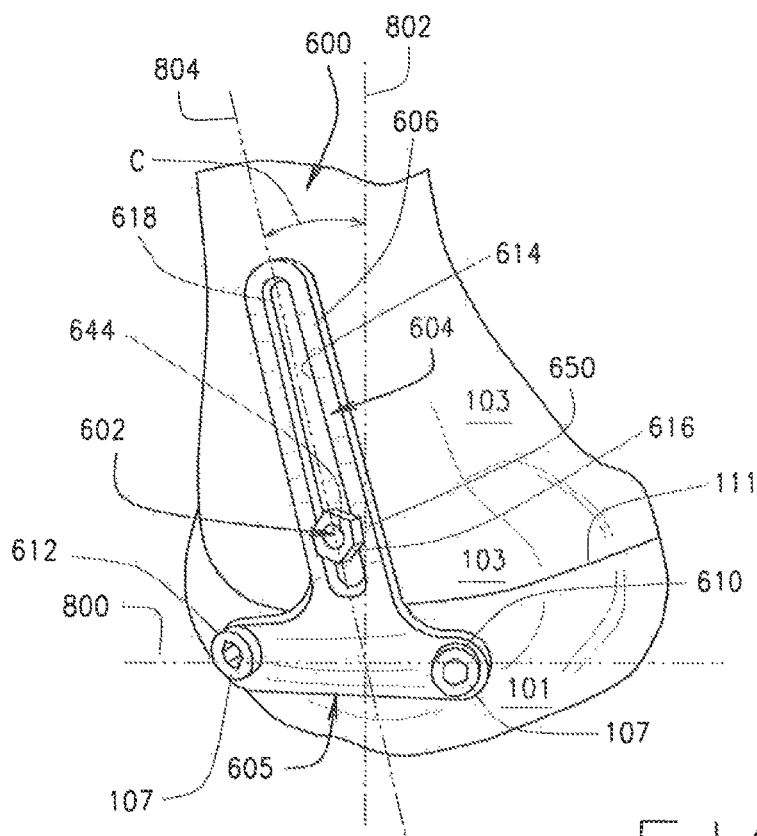
FIG. 12 is a perspective view of the first stationary segment engaged to a bone for the orthopedic apparatus of FIG. 11.

Referring to FIGS. 12-14, one embodiment of a method for using the orthopedic apparatus 600 is illustrated. As shown in FIG. 12, the first stationary segment 604 having a first narrow slot 614 is engaged to the first bone portion 101 by inserting a pair of fastening members 107 through respective openings 610 and 612 such that the first fixed portion 605 of the stationary segment 604 is aligned along a first longitudinal axis 800, which is in perpendicular relation to latitudinal axis 802. In this orientation, the first track portion 606 extends outwardly from the first fixed portion 605 along an axis 804 at a predetermined angle C (FIG. 12) relative to the latitudinal axis 802 (FIGS. 12 and 13). For example, in one embodiment the first track portion 606 extends outwardly at an angle of about 30 degrees relative to the latitudinal axis 802, although in other embodiments predetermined angle C may range between 1 to 89 degrees. As shown in FIG. 13, once engaged, the first stationary segment 604 is used as a guide for forming a channel 620 (FIG. 13) along a second longitudinal axis 806 through the first bone portion 101 at a first position 616. A guide pin (not shown) may be inserted through the channel 620 to align the second stationary segment 604A (FIG. 14). In one embodiment, the channel 620 may be formed using a drill apparatus (not shown) having a drill bit sized and shaped to form the first channel 620. The guide pin may then be removed and the first mobile connector 602 having a first distal end 642 inserted into the first channel 620 such that a first proximal end 644 of the first mobile connector 602 extends outwardly from the first channel 620. A coupling member 650 may then be coupled to the proximal end 644 to secure the first mobile connector 602 within the first channel 620 formed inside the second bone portion 103. In some embodiments, the coupling member 650 may be a nut, such as a hexagonal nut.

Referring back to FIG. 14, the second stationary segment 604A having a second narrow slot 614A is then secured to the first bone portion 101 below the growth plate 111 using a pair of fastening members 107 in the same manner as the engagement of the first stationary segment 604 such that the second narrow slot 614A is in alignment with the channel 620. The first mobile connector 602 and the second mobile connector 602A are then inserted through the first and second narrow slots 614 and 614A, respectively, such that the first and second mobile connectors 602 and 602A are disposed within the channel 620 from opposite directions and the second distal end 646 of the second mobile connector 602A engages the first distal end 642 of the first mobile connector 602. Referring to FIG. 12, a coupling member 650 may be engaged to the second mobile connector 602A to secure the second mobile connector 602A within the channel 620.

As shown in FIG. 13, in some embodiments first and second channels 620 and 622 may be formed from opposite ends of the second bone portion 103, rather than forming a single channel 620 through the entire second bone portion 103 either along the same axis 806 or along different axes for allowing engagement of the first mobile connector 602 to the second mobile connector 602A. As the bone grows, the engaged first and second mobile connectors 602 and 602A will slowly migrate upward along the first and second narrow slots 614 and 614A from a first position 616 (FIG. 13) to a second position 618 (FIG. 14) as the first and second bone portions 101 and 103 grow over time.

Figure 17:
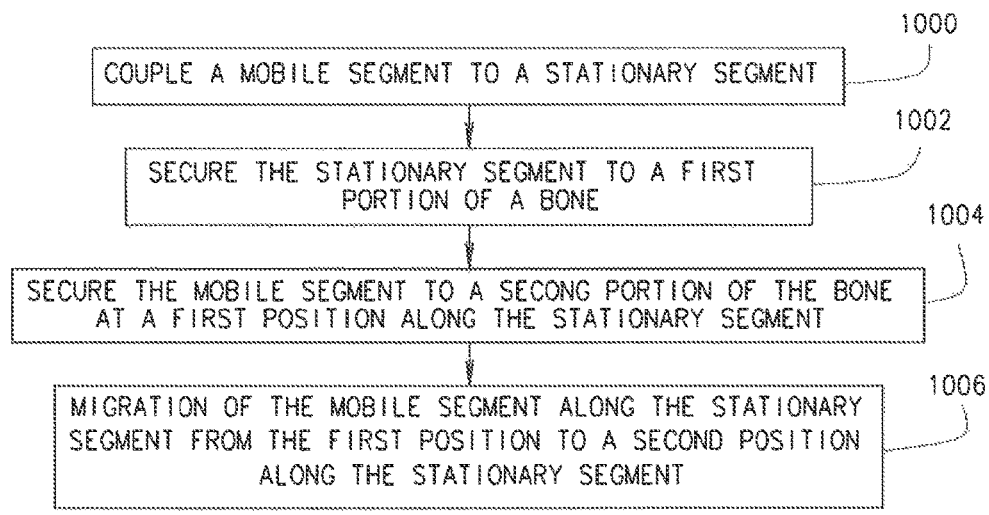
FIG. 17 is a flow chart illustrating a method for using the orthopedic apparatus of FIGS. 1 and 8.

Referring to FIG. 17, a flow chart illustrating one general method for using the orthopedic apparatuses 100 is shown. At block 1000, the mobile segment 102 is coupled to the stationary segment 104. The stationary segment 104 is then secured to a first bone portion 101 at block 1002 and the mobile segment 102 is secured to a second bone portion 103 at the first position 115 at block 1004 in which the first bone portion 101 is separated from the second bone portion 103 by the growth plate 111. In some embodiments, blocks 1002 and 1004 that secure the stationary segment 104 and the mobile segment 102 to the first and second bone portions 101 and 103, respectively, may be performed prior to performing block 1000 in which the mobile segment 102 is coupled to the stationary segment 104. At block 1006, the mobile segment 102 migrates along the stationary segment 104 from the first position 115 to a second position 117 along the stationary segment 104 as the first and second bone portions 101 and 103 grow over time. Although FIG. 17 is described with respect to one general method for using the orthopedic apparatus 100, the same method of use applies to orthopedic apparatus 400.

Figure 18:
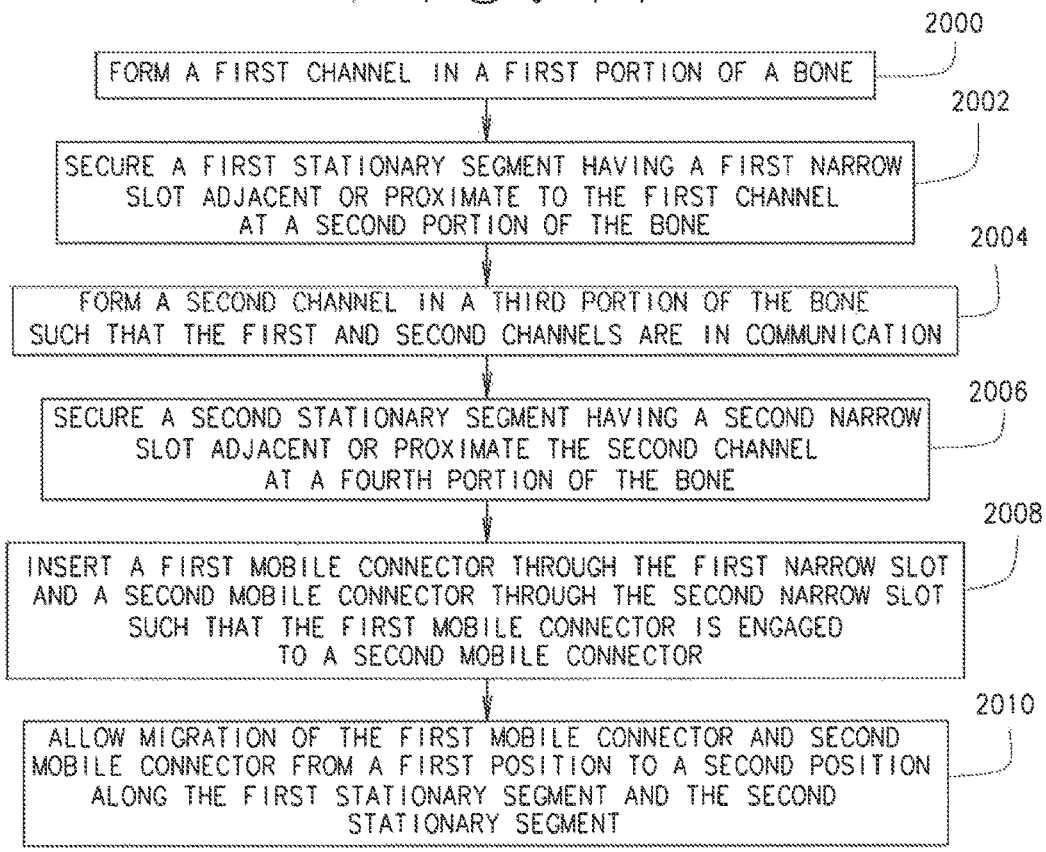
FIG. 18 is a flow chart illustrating a method for using another embodiment of the orthopedic apparatus of FIG. 11.

Referring to FIG. 18, a flow chart illustrating one general method of using the orthopedic apparatus 600 is shown. At block 200'0, a first stationary segment 604 having a first narrow slot 614 is secured to a first bone portion 101. At block 2002, a channel 620 is formed is formed completely through a second bone portion 103 that is in alignment with the first narrow slot 614. As shown, the first bone portion 101 is separated from the second bone portion 103 by a growth plate 111. At block 2004 a second stationary segment 604A having a second narrow slot 614A is secured to the first bone portion 101 generally opposite of the first stationary segment 604 such that the second narrow slot 614A is in alignment with the channel 620 formed between the first and second stationary segments 604 and 604A. At block 2006, a first mobile connector 602 is inserted through a first narrow slot 614 of the first stationary segment 604 and a second mobile connector 602A is inserted through a second narrow slot 614A such that the first mobile connector 602 is engaged to the second mobile connector 602A through the channel 620. At block 2008, the first mobile connector 602 and the second mobile connector 602A are allowed to migrate from a first position 616 to a second position 618 along the first stationary segment 604 and the second stationary segment 604A as the first and second bone portions 101 and 103 grow over time.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An orthopedic apparatus comprising:
    a stationary segment comprising:
        a fixed portion; and
        a track portion that extends from the fixed portion;
    a mobile segment configured to engage and guide the mobile segment along the track portion of the stationary segment; and
    a plurality of fastening members configured to engage the stationary segment to a first bone portion of an individual and the mobile segment to a second bone portion of the individual, wherein the first bone portion and the second bone portion are separated by a growth plate of the individual,
    wherein the track portion includes an angled distal part that angles away from a proximal part of the track portion defined along the fixed portion, the angled distal part extending along a Z-axis such that the angled distal part of the track portion terminates outside a two-dimensional x-y plane defined by the fixed portion, and the mobile segment traverses around lateral edges of the track portion along the Z-axis, the angled distal part of the track portion extending linearly along the Z-axis at a predetermined angle relative to the proximal part of the track portion.

2. The orthopedic apparatus of claim 1, wherein the track portion defines a first groove and a second groove along opposite edges of the track portion.

3. The orthopedic apparatus of claim 2, wherein the track portion defines a narrow slot formed between the first groove and the second groove.

4. The orthopedic apparatus of claim 2, wherein the first groove and the second groove form a linear path that guides the mobile segment along the track portion of the stationary segment.

5. The orthopedic apparatus of claim 1, wherein the body of the mobile segment forms a generally parallelogram configuration.

6. The orthopedic apparatus of claim 1, wherein fixed portion is aligned along a longitudinal axis in perpendicular relation to a latitudinal axis such that the predetermined angle between the axis of the track portion and the latitudinal axis of the fixed portion ranges between 1-89 degrees.

7. The orthopedic apparatus of claim 1, wherein the body of the mobile segment has a curved or bowed configuration that substantially comports to the stationary segment.

8. The orthopedic apparatus of claim 1, wherein the stationary segment has a curved or bowed configuration that substantially comports to the first bone portion and second bone portion.

9. The orthopedic apparatus of claim 3, wherein the narrow slot, the first groove and the second groove each define a respective linear path that guides the mobile segment along the track portion of the stationary segment.

10. The orthopedic apparatus of claim 1, wherein the track portion defines at least a symmetrical-shape configuration or an asymmetrical-shape configuration.

11. The orthopedic apparatus of claim 1, wherein the mobile segment defines an opening configured to receive one of the plurality of fastening members to secure the mobile segment to the second bone portion.

12. The orthopedic apparatus of claim 2, wherein the mobile segment further defines a body having a first retaining member and an opposite second retaining member configured to engage the first groove and the second groove of the track portion and guide the mobile segment along the stationary segment.

13. The orthopedic apparatus of claim 1, wherein the fixed portion defines at least one opening configured to receive one of the plurality of fastening members to secure the stationary segment to the first bone portion of the individual.

14. The orthopedic apparatus of claim 1, wherein the track portion extends from the fixed portion at an acute angle.

15. The orthopedic apparatus of claim 1, wherein the mobile segment further comprises:
    a slot defined by the body between the first retaining member and the opposite second retaining member, the slot being configured to receive the stationary segment.

16. The orthopedic apparatus of claim 1, wherein the mobile segment comprises:
    a guide portion; and
    at least one ring portion extending from the guide portion.

17. The orthopedic apparatus of claim 16, wherein the guide portion comprises:
    a center aperture configured to engage the track portion of the stationary segment.

18. The orthopedic apparatus of claim 17, wherein the center aperture defines at least a circular-shaped configuration, a square-shaped configuration, an oval-shaped configuration, a rectangular-shaped configuration, or an angular-shaped configuration.

19. The orthopedic apparatus of claim 17, wherein the center aperture defines at least a symmetrical or an asymmetrical configuration.

20. The orthopedic apparatus of claim 1, wherein the track portion defines at least a symmetrical shaped configuration or an asymmetrical-shaped configuration.

21. A method of correcting a bone deformity comprising:
    securing a stationary segment to a first bone portion of an individual, the stationary segment comprising:
        a fixed portion oriented at a first longitudinal axis in perpendicular relation to a latitudinal axis, wherein the fixed portion is configured to engage the first bone portion; and
        a track portion defining an angled distal part extending linearly from the fixed portion along an axis at a predetermined angle from the fixed portion;
    coupling a mobile segment to the track portion of the stationary segment, wherein the track portion guides the mobile segment along the stationary segment; and
    securing the mobile segment to a second bone portion,
    wherein the track portion angles away from the fixed portion along a z-axis such that the track portion terminates outside a two-dimensional x-y plane defined by the fixed portion, and the mobile segment traverses around lateral edges of the track portion along the Z-axis.

22. The method of claim 21, further comprising:
    allowing the mobile segment to migrate from a first position along the track portion to a second position along the track portion over a period of time as the first bone portion and the second portion grows.

23. The method of claim 22, wherein the first position corresponds to the engagement of the mobile segment adjacent or proximate to a proximal part of the track portion and the second position corresponds to the engagement of the mobile segment adjacent or proximate to a distal part of the track portion.

* * * * *